US009615951B2

(12) United States Patent
Bennett et al.

(10) Patent No.: US 9,615,951 B2
(45) Date of Patent: *Apr. 11, 2017

(54) MANUAL ACTUATION SYSTEM FOR DEPLOYMENT OF IMPLANT

(71) Applicant: Penumbra, Inc., Alameda, CA (US)

(72) Inventors: Eric Bennett, San Francisco, CA (US);
Erin Vitus, East Palo Alto, CA (US);
Matt Vargas, San Jose, CA (US);
Arani Bose, New York, NY (US);
Stephen Pons, San Francisco, CA (US);
Ben Tompkins, Danville, CA (US);
David Barry, Livermore, CA (US)

(73) Assignee: Penumbra, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/542,001

(22) Filed: Nov. 14, 2014

(65) Prior Publication Data

US 2015/0073524 A1 Mar. 12, 2015

Related U.S. Application Data

(63) Continuation of application No. 12/888,137, filed on Sep. 22, 2010, now Pat. No. 8,911,487.

(Continued)

(51) Int. Cl.
*A61F 2/06* (2013.01)
*A61F 2/95* (2013.01)
*A61M 25/01* (2006.01)

(52) U.S. Cl.
CPC .............. *A61F 2/95* (2013.01); *A61M 25/01* (2013.01); *A61F 2002/9511* (2013.01); *A61M 25/0136* (2013.01); *A61M 25/0147* (2013.01)

(58) Field of Classification Search
CPC .............. A61M 25/01; A61M 25/0147; A61M 25/0136; A01B 12/006; A61F 2/95; A61F 2002/9511; B25G 1/00

(Continued)

(56) References Cited

U.S. PATENT DOCUMENTS 2,934,318 A 4/1960 Schultz
3,018,531 A 1/1962 Jacques (Continued)

FOREIGN PATENT DOCUMENTS

EP 1797833 A1 6/2007

OTHER PUBLICATIONS

International search report and written opinion dated Nov. 26, 2010 for PCT/US2010/049847.

(Continued)

*Primary Examiner* — Amy R Weisberg
(74) *Attorney, Agent, or Firm* — Wilson Sonsini Goodrich & Rosati

(57) ABSTRACT

A system for mechanically deploying intraluminal implants is disclosed. The system is used with an implant that is delivered and/or deployed via a pull wire and includes a handle having a funnel and receiving channel for receiving the pull wire, a slider having a thumb grip and a wedge, and a shuttle having a grabber for grasping the pull wire. The thumb grip is pulled proximally to retract the wedge to cause the grabber to grasp the wire and retract the shuttle but not the wire. An extension spring linked between the slider and the shuttle abruptly pulls the shuttle to retract the pull wire after the slider is fully retracted.

16 Claims, 9 Drawing Sheets

FIG. 2B

Related U.S. Application Data

(60) Provisional application No. 61/244,785, filed on Sep. 22, 2009.

(58) Field of Classification Search
USPC ...... 623/1.11–1.12, 2.11; 606/108, 213, 215, 606/232, 103, 74; 600/585; 294/132, 294/135–136, 104; 254/134.3 R; 81/490
See application file for complete search history.

(56) References Cited

U.S. PATENT DOCUMENTS

| | | | |
|---|---|---|---|
| 3,312,128 A | 4/1967 | Wasson | |
| 3,467,102 A | 9/1969 | Forgarty et al. | |
| 4,799,496 A | 1/1989 | Hargreaves et al. | |
| 4,860,776 A | 8/1989 | McQuain | |
| 5,219,332 A | 6/1993 | Nelson et al. | |
| 5,261,916 A | 11/1993 | Engelson | |
| 5,273,042 A | 12/1993 | Lynch et al. | |
| 5,304,195 A | 4/1994 | Twyford, Jr. et al. | |
| 5,312,338 A | 5/1994 | Nelson et al. | |
| 5,325,746 A | 7/1994 | Anderson | |
| 5,325,868 A | 7/1994 | Kimmelstiel | |
| 5,350,397 A | 9/1994 | Palermo et al. | |
| 5,431,370 A | 7/1995 | Verkuylen et al. | |
| 5,438,993 A | 8/1995 | Lynch et al. | |
| 5,443,477 A | 8/1995 | Marin et al. | |
| 5,499,990 A | 3/1996 | Schulken et al. | |
| 5,579,780 A | 12/1996 | Zadini et al. | |
| 5,749,371 A | 5/1998 | Zadini et al. | |
| 5,782,909 A | 7/1998 | Quiachon et al. | |
| 5,800,454 A | 9/1998 | Jacobsen et al. | |
| 5,853,418 A | 12/1998 | Ken et al. | |
| 5,891,058 A | 4/1999 | Taki et al. | |
| 5,891,130 A | 4/1999 | Palermo et al. | |
| 5,895,391 A | 4/1999 | Farnholtz | |
| 5,902,305 A | 5/1999 | Beger et al. | |
| 5,935,141 A | 8/1999 | Weldon | |
| 5,968,052 A | 10/1999 | Sullivan, III et al. | |
| 6,039,744 A | 3/2000 | Forber | |
| 6,042,585 A | 3/2000 | Norman | |
| 6,231,564 B1 | 5/2001 | Gambale | |
| 6,344,044 B1 | 2/2002 | Fulkerson et al. | |
| 6,391,030 B1 | 5/2002 | Wagner et al. | |
| 6,391,051 B2 | 5/2002 | Sullivan, III et al. | |
| 6,488,700 B2 | 12/2002 | Klumb et al. | |
| 6,533,772 B1 | 3/2003 | Sherts et al. | |
| 6,544,267 B1 | 4/2003 | Cole et al. | |
| 6,551,340 B1 | 4/2003 | Konya et al. | |
| 6,599,296 B1* | 7/2003 | Gillick et al. | 606/108 |
| 6,663,588 B2 | 12/2003 | DuBois et al. | |
| 6,808,529 B2 | 10/2004 | Fulkerson | |
| 7,326,236 B2 | 2/2008 | Andreas et al. | |
| 7,377,932 B2 | 5/2008 | Mitelberg et al. | |
| 7,497,853 B2 | 3/2009 | Fischer | |
| 7,550,001 B2 | 6/2009 | Dorn et al. | |
| 7,585,311 B2 | 9/2009 | Green et al. | |
| 7,674,282 B2 | 3/2010 | Wu et al. | |
| 7,713,275 B2 | 5/2010 | Greenberg et al. | |
| 7,717,865 B2 | 5/2010 | Boutillette et al. | |
| 7,753,917 B2 | 7/2010 | Urbanski et al. | |
| 7,758,625 B2 | 7/2010 | Wu et al. | |
| 7,887,549 B2 | 2/2011 | Wenderow et al. | |
| 7,976,574 B2 | 7/2011 | Papp | |
| 8,043,301 B2 | 10/2011 | Adams et al. | |
| 8,070,694 B2 | 12/2011 | Galdonik et al. | |
| 8,096,998 B2 | 1/2012 | Cresina | |
| 8,333,796 B2 | 12/2012 | Tompkins et al. | |
| 8,500,789 B2 | 8/2013 | Wuebbeling et al. | |
| 8,540,215 B2* | 9/2013 | Iwama | B25B 25/00 24/134 R |
| 8,911,487 B2 | 12/2014 | Bennett et al. | |
| 2004/0186511 A1* | 9/2004 | Stephens et al. | 606/200 |
| 2005/0192621 A1 | 9/2005 | Wallace et al. | |
| 2006/0243341 A1* | 11/2006 | Bernard | B65B 13/24 140/123.5 |
| 2007/0088421 A1* | 4/2007 | Loewen | 623/1.11 |
| 2007/0121405 A1 | 5/2007 | Ueno | |
| 2007/0179520 A1 | 8/2007 | West | |
| 2007/0293928 A1 | 12/2007 | Tomlin | |
| 2008/0097462 A1 | 4/2008 | Mitelberg et al. | |
| 2009/0210046 A1 | 8/2009 | Shumer et al. | |
| 2009/0270877 A1 | 10/2009 | Johnson et al. | |
| 2010/0174269 A1 | 7/2010 | Tompkins et al. | |
| 2010/0229698 A1* | 9/2010 | Shawcross | B25B 25/00 81/486 |
| 2011/0238147 A1* | 9/2011 | Bennett et al. | 623/1.11 |
| 2013/0018359 A1* | 1/2013 | Coyle | 604/528 |
| 2013/0317592 A1 | 11/2013 | Wubbeling et al. | |
| 2014/0358156 A1* | 12/2014 | Argentine | 606/108 |

OTHER PUBLICATIONS

Notice of allowance dated Aug. 22, 2014 for U.S. Appl. No. 12/888,137.
Office action dated Apr. 11, 2013 for U.S. Appl. No. 12/888,137.
Office action dated Dec. 4, 2012 for U.S. Appl. No. 12/888,137.

* cited by examiner

MANUAL ACTUATION SYSTEM FOR DEPLOYMENT OF IMPLANT

CROSS-REFERENCES TO RELATED APPLICATIONS

This application is a continuation of U.S. patent application Ser. No. 12/888,137, filed Sep. 22, 2010, now U.S. Pat. No. 8,911,487, which claims priority to Provisional Application 61/244,785, filed Sep. 22, 2009, the disclosures of which are incorporated herein by reference in their entirety.

BACKGROUND OF THE INVENTION

Field of the Invention

The present invention relates generally to systems and methods for implanting intravascular devices, and more specifically to manual systems and methods for mechanically releasing, detaching or otherwise deploying devices within a body lumen.

Numerous intravascular implant devices are well known in the field. Many are deployed mechanically, via systems that combine one or more catheters and wires for delivery. Examples of implants that may be delivered mechanically include embolic coils and other elements, stents, grafts, drug delivery implants, and the like. Some obstetric and gastrointestinal implants may also be implanted endolumenally via similar means. Devices that may be released or deployed by mechanical means vary greatly in design, but may employ a similar delivery catheter and wire system. Many such catheter-based delivery systems include a wire for retention of the implant in the catheter until the time for release of the device. These systems are then actuated by retracting or pulling the wire relative to the catheter. Such a wire is referred to herein as a "pull wire". Examples of implants delivered via catheter and released via a pull wire are described in more detail in U.S. patent application Ser. No. 12/498,752, which is incorporated by reference as if set forth herein in its entirety.

Precise control of the timing of deployment of the implant is crucial for the successful treatment of vascular and luminal abnormalities. Premature release of an implant can lead to injury and death. The timing of deployment of the implant is under the control of an operator who will retract the pull to release the implant from the distal end of the catheter. The force applied and speed of action will vary among operators, and a single operator may apply force inconsistently.

Because of the foregoing needs, it is an object of the invention to confer consistent force and speed of release in deployment of a delivery system. It is a further object of the invention to achieve reliable and consistent delivery and deployment of an implant released utilizing a pull wire system. At least some of these objectives will be met by the inventions set forth below.

BRIEF SUMMARY OF THE INVENTION

An actuation system according to the present invention is intended for use with an implant delivery system that employs a catheter and a pull wire for release of the implant. In a typical procedure utilizing the invention, an implant is loaded into the distal end of a catheter or comparable implant tool. The pull wire is disposed through the length of the catheter with a distal end retaining the implant near the distal end of the catheter and a proximal end remaining in control of the operator. The catheter is then introduced, for example, into the femoral artery and navigated through the vascular system under fluoroscopic visualization. The distal end of the catheter is positioned at the proposed treatment site within the vasculature or other luminal structure of a subject. The treatment site may be, for example, an aneurysm, an arterio-venous malformation, an occlusion, or other defect. Once positioned, the pull wire is retracted relative to the catheter, typically manually, and the implant is released from the catheter distal end and to the particular treatment site. Once released from the catheter, the implant may for example assume a secondary shape selected to optimize treatment, such as filling of an aneurysm cavity, or alternatively, re-establishing patency of a vessel. In some cases, multiple implants may be introduced to a single treatment site, optionally using the same actuation system with multiple delivery catheters.

In a first aspect of the present invention, a handle for retracting a pull wire disposed in a catheter body comprises a shell having a distal end, a proximal end, and a receptacle at the distal end for receiving a proximal end of the catheter body. A trigger is slidably mounted on an exterior of the shell, and a slider carrying a tripping element is disposed within the shell and coupled to move with the trigger. A shuttle is also slidably disposed within the shell and is coupled to the slider by a first energy storage member, such as an elongate coil spring, where the shuttle carries a wire grabber at its distal end and has a latch member releasably engageable with a stop member fixed to the shell, typically on an inside surface of the shell. Proximal retraction of the trigger by a physician or the user draws the slider proximally within the handle, storing potential energy in the first energy storage member. The stop member immobilizes the shuttle until the tripping element on the slider engages and releases the latch from the stop element, thus allowing the shuttle to be abruptly pulled proximally by release of energy from the first energy storage member, e.g., contraction of the coil springs. In this way, the physician or other user can smoothly pull back the trigger to store sufficient energy to provide the rapid retraction of the pull wire which is desired.

Usually, the slider will be further adapted to open the wire grabber to release the pull wire when the trigger is fully returned to its initial position. Such decoupling of the pull wire is a safety feature which reduces the risk of inadvertently moving the pull wire to dislodge the implant or otherwise have a deleterious effect. Such automatic release of the wire grabber also resets the handle for use with another catheter and pull wire.

In a further preferred aspect, initial proximal refraction of the trigger will close the wire grabber to engage the pull wire. Thus, the physician or other user need only insert a proximal end of the catheter into the receptacle at the end of the shell to position the pull wire in the grabber. Engagement of the pull wire then occurs automatically as the trigger is initially retracted.

The shuttle is initially immobilized relative to the handle by a locking or latching mechanism. The locking mechanism typically comprises a lever pivotally mounted on the shuttle and having a surface which is engaged by a wedge on the slider to open the latch to release the stop when the trigger is fully retracted in the proximal direction.

The first energy storage member typically comprises an elastic extension member, typically an elongate coil spring, mounted between the slider and the shuttle so that it elongates as the trigger is proximally retracted. The handle assembly will typically include a second energy storage member coupled between the slider and the shell such that proximal refraction of the trigger stores potential energy in the second energy storage member to return the slider to its distal most position when the trigger is released. Usually, the second energy storage member will be a coil compression spring.

In a second aspect of the present invention, a method for retracting a pull wire in a catheter, typically to release an implant, comprises mating a proximal end of the catheter with a handle. A trigger on the handle is then proximally retracted to proximally translate a slider in the handle to perform the following steps in sequence. First, a grabber disposed on a shuttle is caused to capture a proximal end of the pull wire. Second, potential energy is stored in a first energy storage device coupled between the slider and the shuttle as the slider is proximally retracted. Third, the shuttle is released so that it can be pulled proximally by the energy storage device in order to retract the pull wire relative to the catheter.

Typically, mating the catheter to the handle comprises aligning a proximal end of the catheter body in a conical receptacle at a distal end of the handle so that the pull wire extends through an opening at the apex of the conical receptacle to pass into the handle. The grabber will typically have a spring-loaded, pivotally mounted lever which closes on the pull wire as a wedge on the slider retracts relative to the shuttle. Thus the pull wire which extends into the handle can be automatically grasped as a trigger is retracted to move a slider relative to the shuttle.

Usually, the shuttle is initially held in place by a latch on the shuttle which engages a stop on the handle. The shuttle is subsequently released by a trip on the slider which engages and dislodges the latch when the slider is retracted proximally by a pre-selected distance, where the distance is selected to store an appropriate amount of energy in the energy storage device. After release of the pull wire, the trigger may be released so that the slider and shuttle return to their distal-most position and the grabber releases the wire. Typically, the slider and shuttle are caused to return to their distal-most position by the release of energy from a second energy storage device disposed between the slider and the handle, where the second energy storage device had stored potential energy as the trigger was initially retracted.

DETAILED DESCRIPTION OF THE INVENTION

Figure 1:
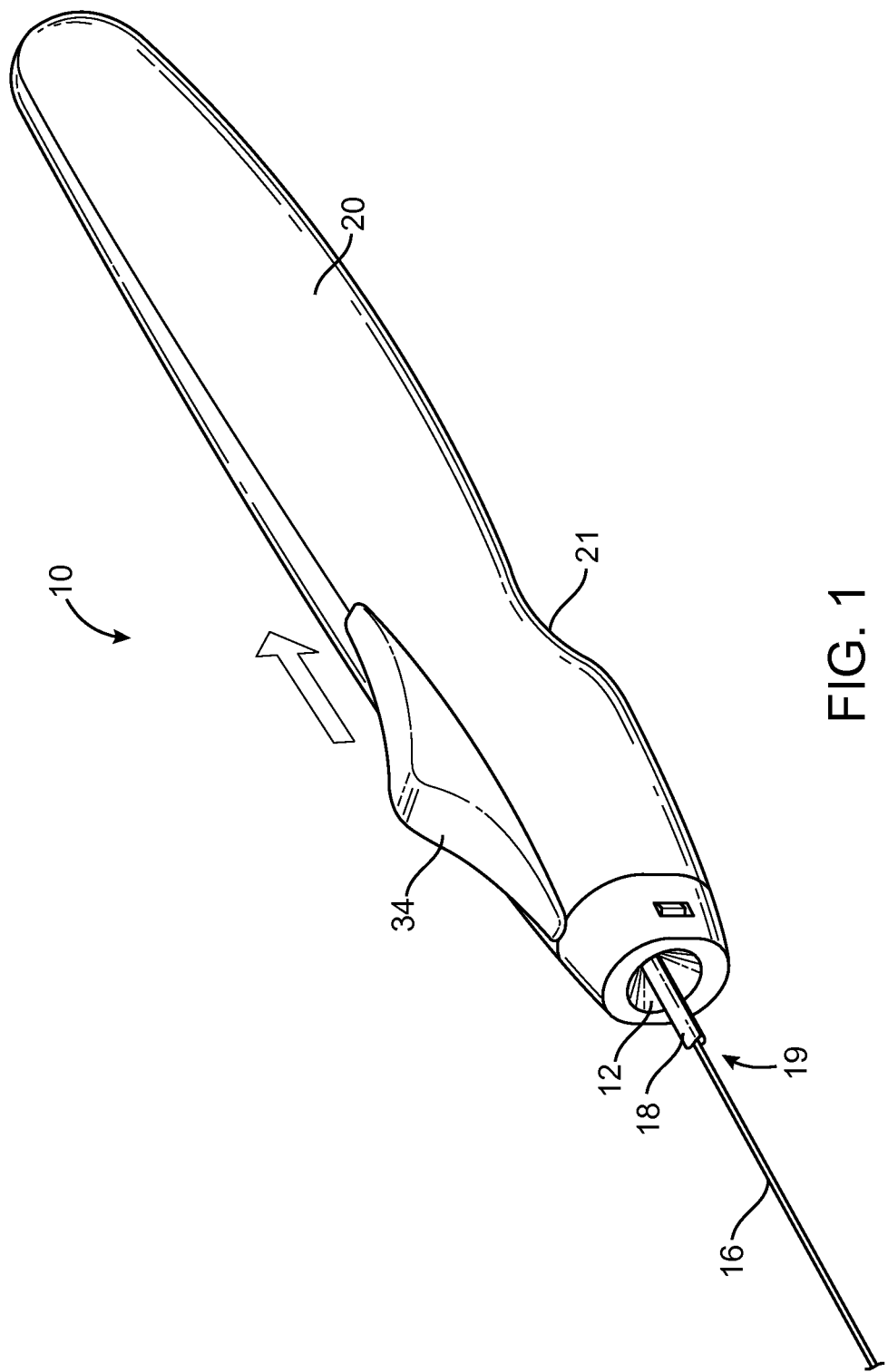
FIG. 1 is a perspective view of an embodiment according to the invention.

Referring to FIG. 1, general components of actuation system 10 are illustrated. When in use, actuation system 10 is releasably attached to a proximal end of an endolumenal implant delivery system such as catheter 19, or a comparable implant delivery tool having a shaft and a lumen, such as a hypotube, or catheter body 18. A pull wire 16 is disposed axially in catheter body 18. System 10 is held and operated by a practitioner during a procedure to implant one or more devices into the vasculature of a patient. As described in further detail below, system 10 includes a handle 20 which houses mechanisms for grasping a proximal end of the pull wire 16, and then abruptly retracting the pull wire 16 upon actuation by a user. Operation may be effected by a single pull by the practitioner's thumb and the implant is thereby deployed in a decisive, consistent, and reliable manner regardless of variations in speed and force applied by the user.

In order to use system 10, an implant is loaded into the catheter 19 or comparable implant tool (such as, for example, the coil delivery catheter described in commonly owned, copending application Ser. No. 12/498,752, previously incorporated herein by reference). A pull wire 16 extends through the lumen of catheter body 18. The proximal end of catheter body 18 is positioned at the apex of a funnel 12, which is formed in a distal end of handle 20, and the proximal end of the pull wire is loaded through funnel 12 and into the distal end of handle 20. Distal end of catheter 19 is inserted into the body, and the implant is carried until the implant and the distal end of catheter 19 are properly positioned in a blood vessel or other body lumen, for deployment of the implant in the body. Although the term "wire" is used herein, it will be understood that any elongated filament of suitable mechanical properties and structure is included in the term.

Figure 2A:
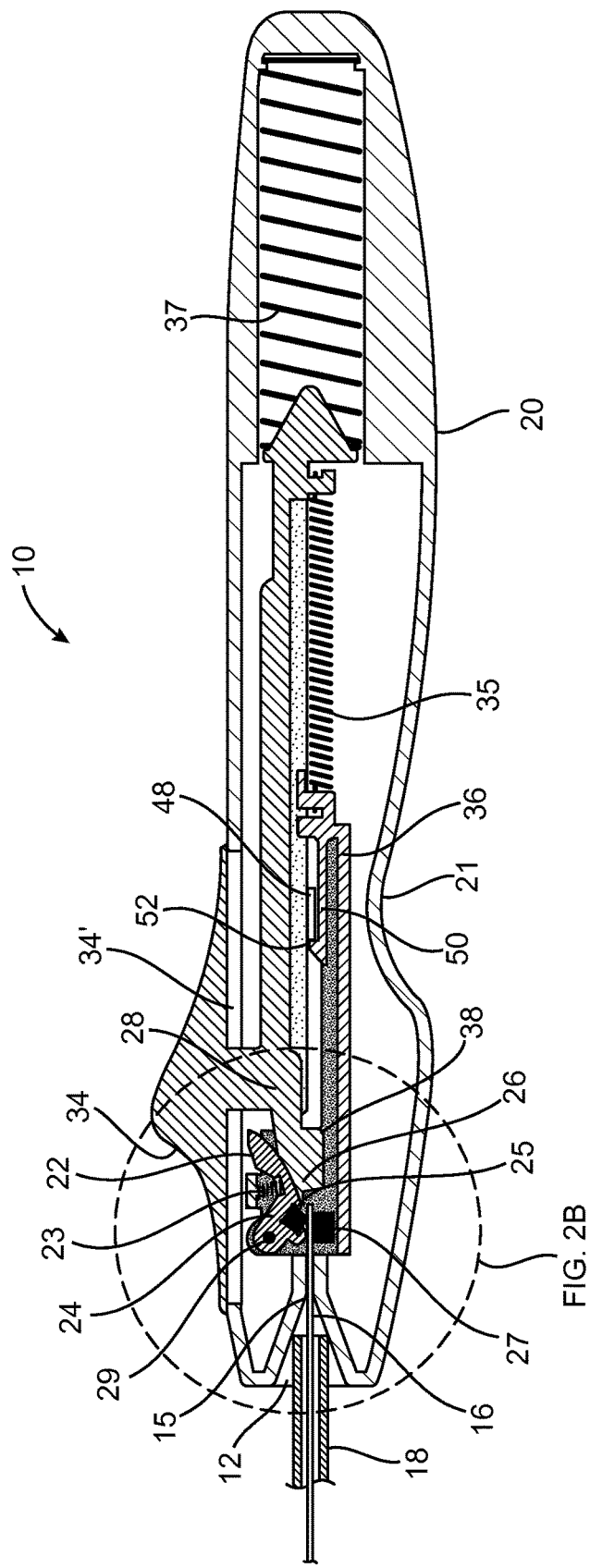
FIG. 2A is a cross-sectional side view of an embodiment according to the invention in a first configuration.
Figure 2B:
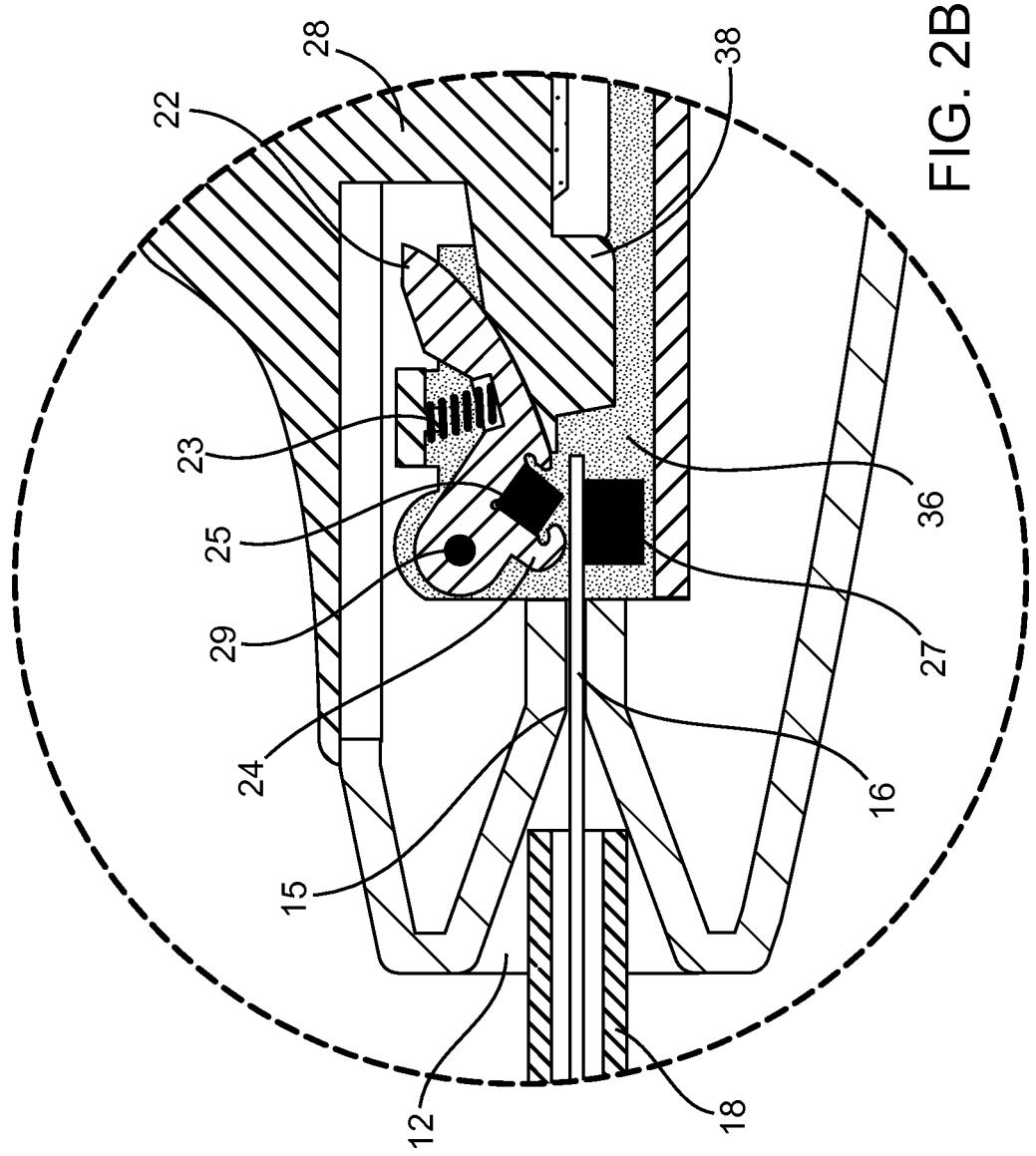
FIG. 2B is an area of detail of FIG. 2A.

While other configurations are within the scope of the invention, handle 20 advantageously includes a finger groove 21 defined by the exterior of handle 20. Also disposed on the exterior of handle 20 is a trigger configured as a thumb grip 34, which is axially movable along the exterior of handle 20 via a channel 34' or comparable structure (FIG. 2A). Applicants use the terms trigger and thumb grip interchangeably herein. Thumb grip 34 may be pulled may be pulled in a proximal direction as indicated by the arrow in FIG. 1 in order to release or otherwise deploy the implant loaded from the distal end of the catheter 19 (as described in commonly owned, copending application Ser. No. 12/498,752, previously incorporated by reference). Thumb grip 34 and handle 20 may be shaped as illustrated in FIG. 1 or otherwise suitably configured to optimize ergonomic functioning. Similarly, handle 20 may be of any dimensions suitable for optimal handling by a user.

Handle 20 may be manufactured from a suitable medical grade plastic, such as Santoprene medical grade Thermoplastic Vulcanizate available from ExxonMobil Chemical, or acrylonitrile butadiene styrene (ABS) available from Lustran. Suitable materials include materials that may be sterilized in ethylene oxide or radiation, or in an autoclave. Further, desirable materials include those that are injection moldable and recyclable. The external surfaces of handle 20 are preferably smooth and non-abrasive. The internal components of handle 20 may be manufactured from polycarbonate and silicone available from RTP Co. or similar materials and may additionally include stainless steel, rubber or other suitable materials. Manual actuation system 10 may include additional elements, materials and coatings for securing the components and for smooth inter-operative engagement of the components.

Figure 3A:
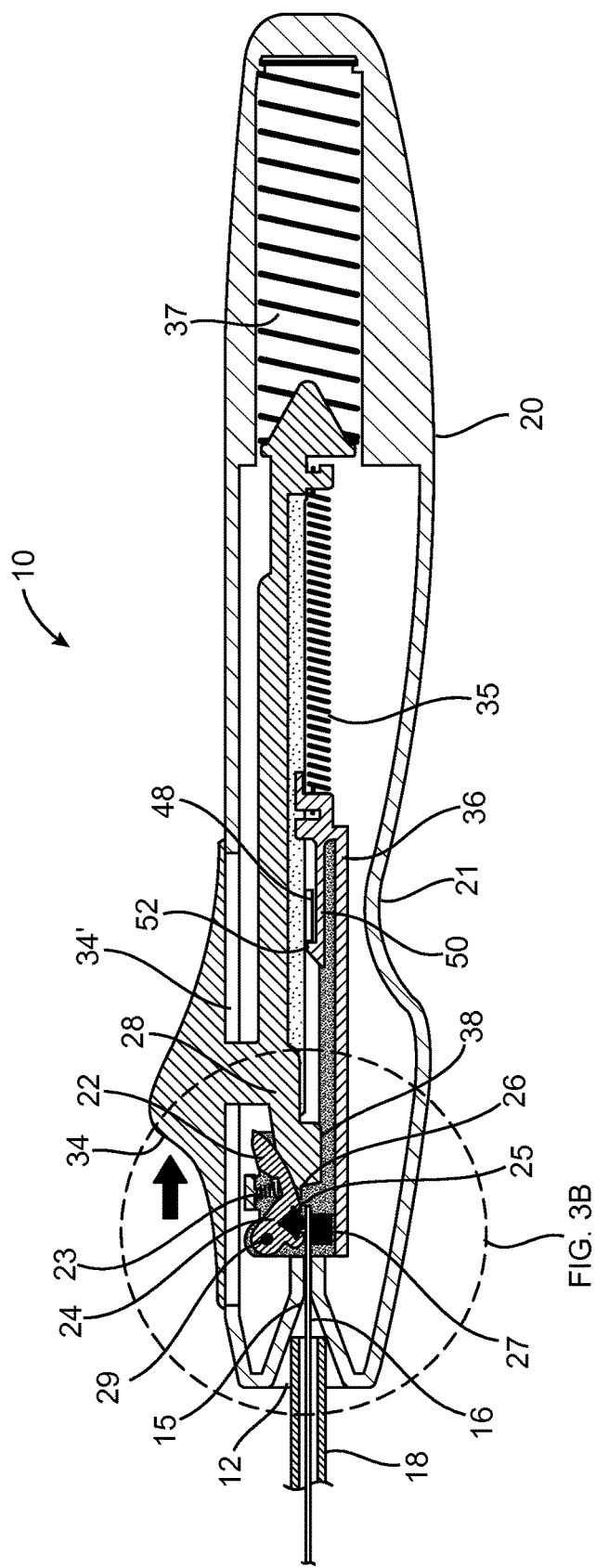
FIG. 3A is a cross-sectional side view of an embodiment according to the invention in a second configuration.
Figure 3B:
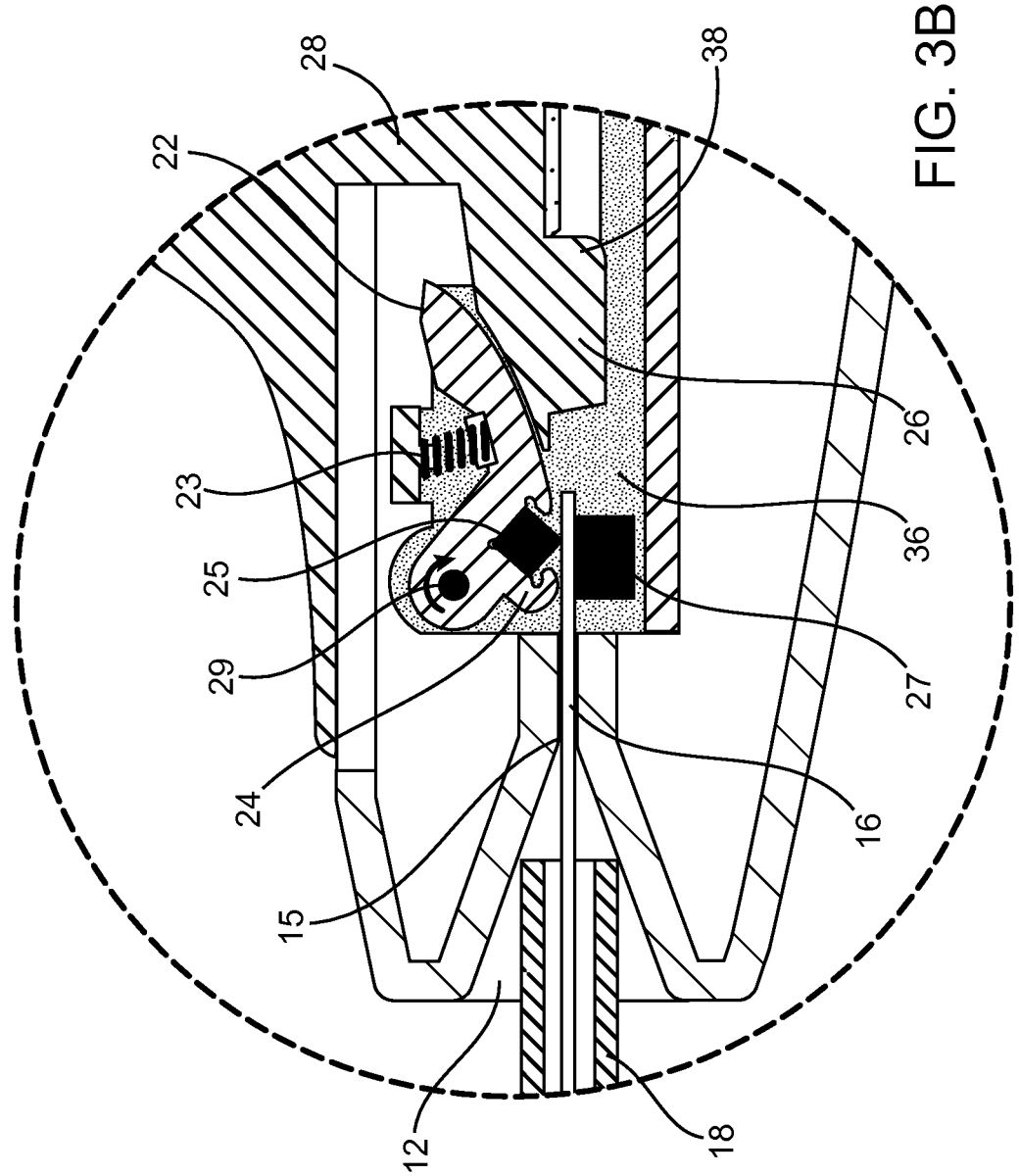
FIG. 3B is an area of detail of FIG. 3A.
Figure 4A:
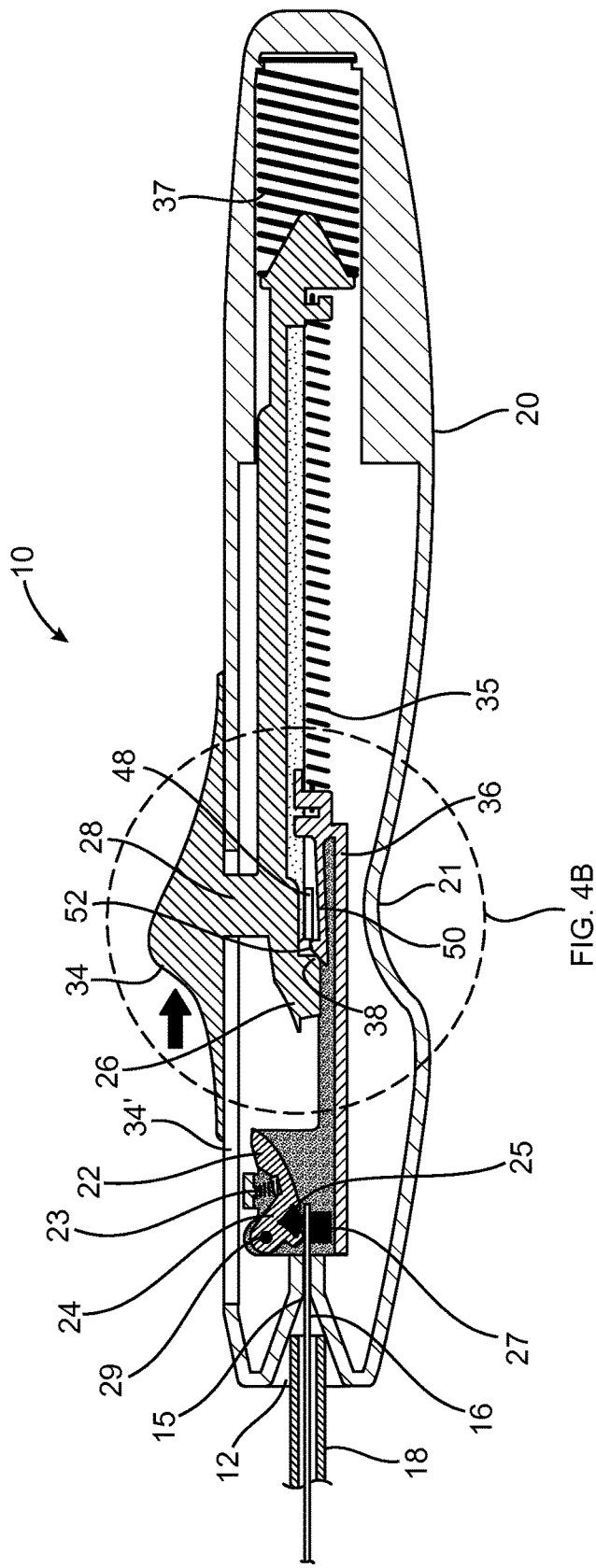
FIG. 4A is a cross-sectional side view of an embodiment according to the invention in a third configuration.
Figure 4B:
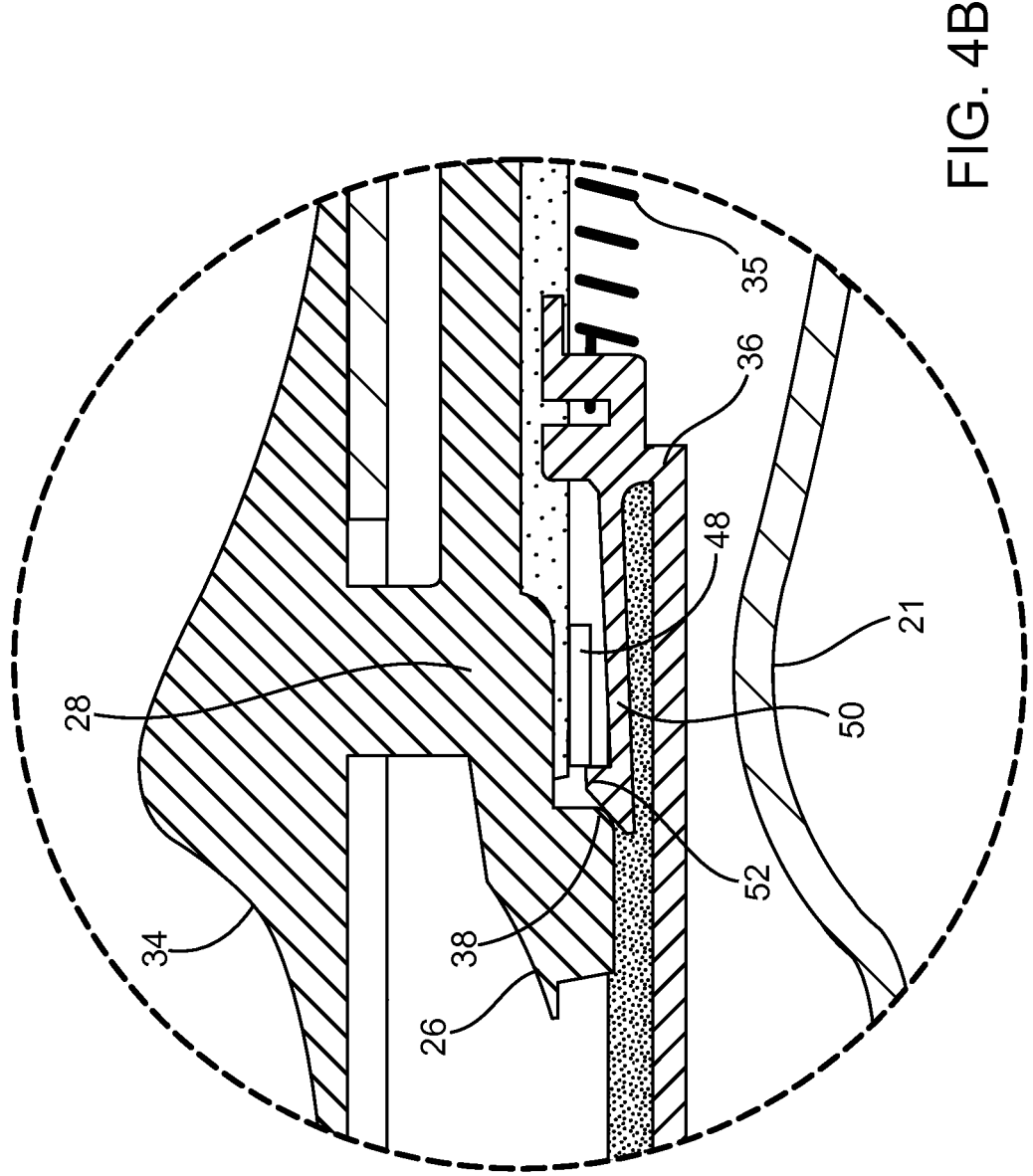
FIG. 4B is an area of detail of FIG. 4A.
Figure 5A:
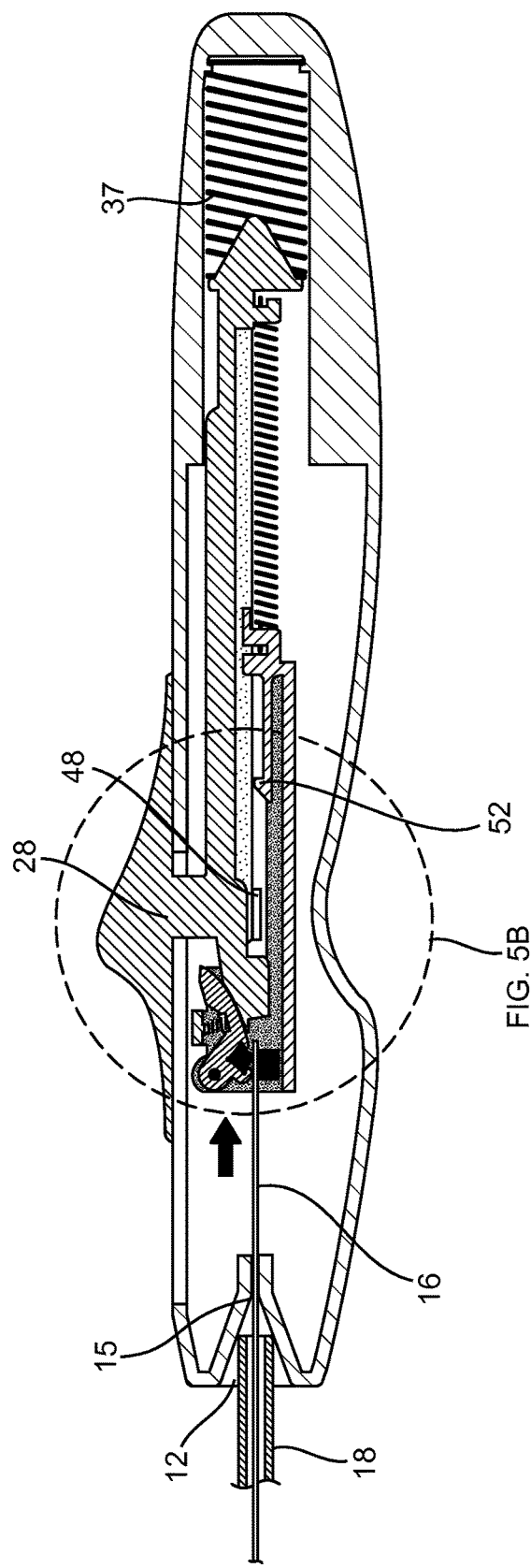
FIG. 5A is a cross-sectional side view of an embodiment according to the invention in a fourth configuration.
Figure 5B:
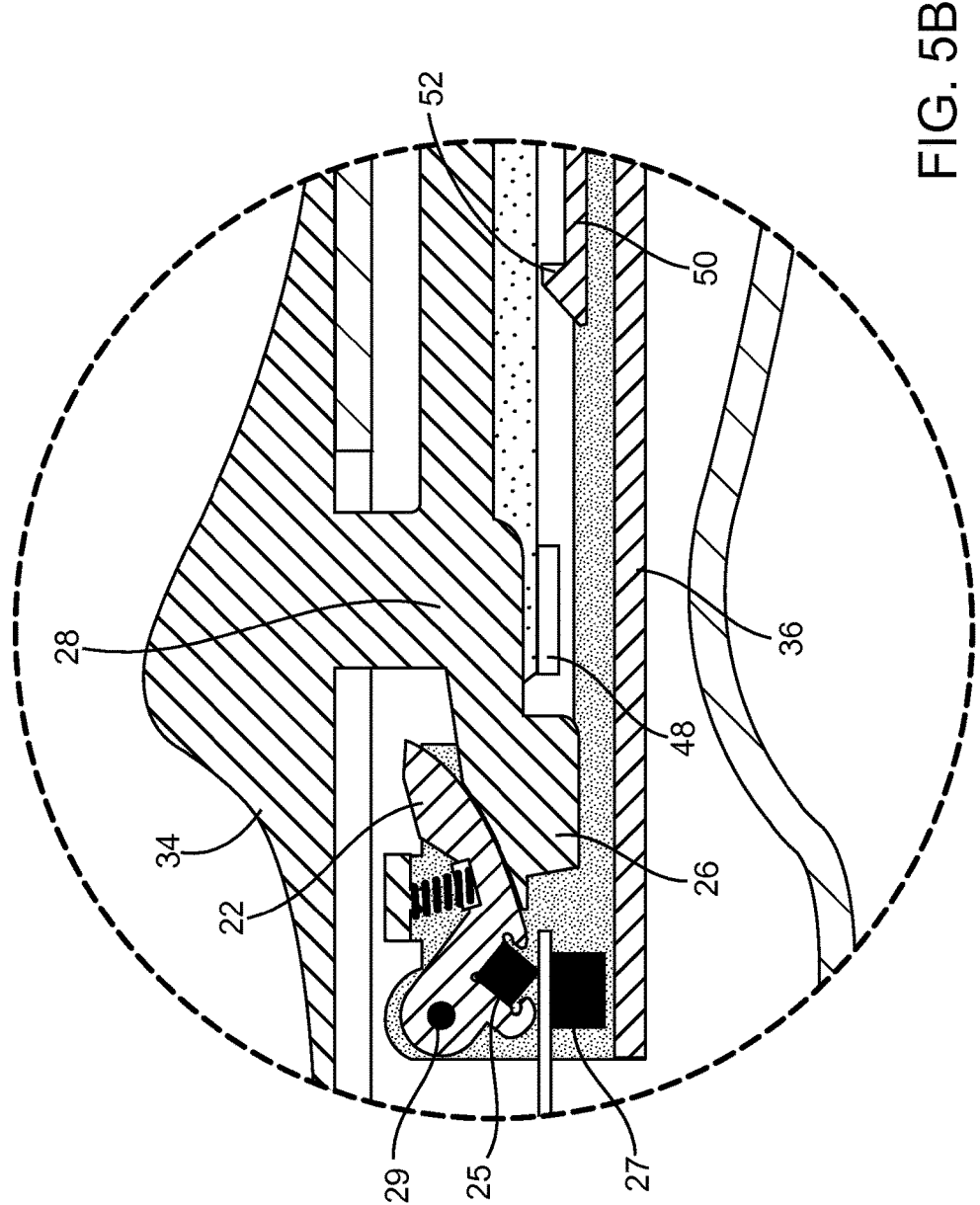
FIG. 5B is an area of detail of FIG. 5A.

An overview of the operation of handle 20 is as follows. FIGS. 2A-5B illustrate "snapshots" taken throughout the sequence of operational steps of system 10. They highlight the most significant transition points of the interaction of the components of system 10, during the retraction of thumb grip 34. In reality, there are an infinite number of configurations of the working components of handle 20, but the range of configurations can be divided into separate phases. A first phase can be referred to as a "resting position", in which thumb grip 34 is not retracted and lies in its distal-most position, as illustrated in FIG. 2A, and in detail in FIG. 2B. A "grasping position" in which thumb grip 34 is slightly retracted in the proximal direction (indicated by the arrow) is illustrated in FIG. 3A, and in detail in FIG. 3B. After the pull wire 16 is grasped, thumb grip 34 is pulled through a longer "priming phase", until it reaches a latch release position (FIGS. 4A-4B). Following latch release, pull wire 16 is abruptly pulled proximally (FIGS. 5A-5B), and the system 10 returns to the initial resting position following release of thumb grip 34. The pull wire 16 is automatically released from the grabber and the handle is ready for use with another catheter or delivery device.

A more detailed description of these separate phases of operation of system 10, with reference again to FIGS. 2A-5B, includes an overview of the changes in configuration of the mechanisms of system 10 throughout these phases. The principle internal components of handle 20 are wire gripper or grabber 24, slider 28, and shuttle 36. In the "at rest" position, wire gripper or grabber 24 is lifted "open" for receiving pull wire 16 between grabber elements 25 and 27 which are mounted on shuttle 36. In the "grasping position" grabber elements 25 and 27 are allowed to close on the proximal end of pull wire 16, thus coupling the pull wire to the shuttle 36. During the priming phase, the trigger, or thumb grip 34 is proximally retracted to pull slider 28 axially along handle 20, but shuttle 36 and grabber 24 remain latched to the handle 20 and stationary until slider 28 triggers release of the latch which allows the shuttle to be drawn in a proximal direction by a spring mechanism which, because the shuttle is coupled to grabber 24, abruptly retracts pull wire 16.

The features of the primary mechanisms can be described as follows, though it will be understood that other configurations are possible according to the invention. The "at rest" and "grasping" positions result from interaction between parts of grabber 24 and slider 28. As shown in FIG. 2A, grabber 24 includes a rocker arm 22 pivotally connected to shuttle 36 via a pivot point 29. A spring 23 biases rocker arm 22 to rotate in a clockwise direction to a "closed position". However, when at rest (prior to initial proximal retraction of the thumb slide 34), grabber 24 is held "open" with grabber element 25 lifted away from grabber element 27 by a wedge 26 carried by slider 28. An upper surface of wedge 26 engages a lower surface of rocker arm 22, biasing rocker arm 22 upwardly against the force of spring 23. While the grabber 24 is thus open, the proximal end of pull wire 16 is loaded through a passage 15 at the apex of the funnel 12 into the distal end of handle 20. The proximal end of catheter 18 is received within funnel 12 but blocked from entry into the handle 20 by channel 15 which is sized to allow the pull wire but not the catheter to pass through.

An initial, slight retraction of thumb grip 34 (in the direction of the proximal direction indicated by the arrow on FIG. 3A) removes the wedge 26 from beneath the rocker arm 22 and allows grabber 24 to grasp the proximal end of wire 16. Though the change in configuration between "at rest" and "grasping" is quite subtle, the grasping configuration is illustrated in FIG. 3A and in detail in FIG. 3B. Slider 28 is linked to thumb grip 34. Slider 28 has a wedge 26. After slight retraction of thumb grip 34, slider 28 travels axially, and wedge 26 also travels axially, out of nesting engagement with grabber 24. In turn, retraction of wedge 26 permits spring 23 to bias rocker arm 22 pivotally about pivot point 29. Grabber element 25 and grabber element 27 can thereby engage or "grasp" wire 16. Note that while the slider 28, wedge 26, and thumb grip 34 are illustrated as a monolithic structure, they could be provided as separate components which are joined or connected by conventional techniques. For the purposes of the present invention, it is important only that they are sufficiently coupled so that they travel in unison as the thumb grip is retracted and later advanced.

Following grasping of the pull wire, further retraction of thumb grip 34 serves to "prime" system 10 for launch of shuttle 36. During the "priming" phase, the wire gripper, or grabber 24 remains stationary, along with pull wire 16 and shuttle 36. Shuttle 36 (now stationary) is linked to slider 28 (which is being retracted), via extension spring 35. During retraction of slider 28, extension spring 35 is progressively stretched, and potential "retraction" energy within extension spring 35 is increasing. Shuttle 36 remains stationary because it is coupled by a button 52 to a stop 48 formed on or attached to an inner surface of the housing that forms handle 20. Priming of the system continues as thumb grip 34 is retracted proximally until a trip 38 on a lower distal portion of slider 28 engages and depresses the button 52 to release button 52 from the stop 48, allowing the shuttle 36 to be drawn proximally by spring 35 (as illustrated in FIGS. 4A-4B).

Button 52 extends from latch member 50, which is cut within a sidewall or otherwise disposed upon shuttle 36. When system 10 is at rest, and during the priming phase, button 52 rests against stop 48. With respect to slider 28, a trip 38 is defined by the proximal end of wedge 26. Trip 38, as a matter of course, travels proximally with slider 28 during retraction of slider 28. When slider 28 is retracted to the point that trip 38 reaches button 52, trip 38 acts to depress button 52 via latch member 50, thereby releasing button 52 from its resting position against stop 48. (See FIGS. 4A-4B). The release of button 52 permits the spring action of extension spring 35, which thereby 'launches' shuttle 36 in a proximal direction within handle 20. (See FIGS. 5A-5B.) And because pull wire 16 is within the grasp of grabber 24, this decisive retraction of shuttle 36 also decisively retracts pull wire 16. And upon the decisive retraction of pull wire 16, the implant (not pictured) is deployed.

Referring back to the "priming" phase, during extension of spring 35, a compression spring 37 is increasingly compressed, and compressive force increases within compression spring 37. Following the launching phase, the user may then release thumb grip 34. Upon release of thumb grip 34, the tension stored in compression spring 37 acts to return slider 28 and shuttle 36 to a neutral position, shown in FIG. 2A. As full distal travel of the slider 28 causes the wedge 26 to engage and lift the rocker arm 22. The pull wire 16 is released. This is both a safety feature as detachment of the actuation system 10 from the catheter or other delivery system reduces the risk of inadvertently disturbing the deployed implant as well as a convenience since the handle is then ready to repeat the foregoing process if desired.

While the invention may be modified and alternative forms may be used, specific embodiments of the invention have been illustrated and described in detail. It should be understood, however, that the description herein of specific embodiments is not intended to limit the invention to the particular forms disclosed. The invention and following claims are intended to cover all modifications and equivalents falling within the spirit and scope of the invention.

What is claimed is:

1. A handle for retracting a pull wire, the handle comprising:
   a shell having a distal end, a proximal end, a stop element, and a receptacle for receiving the proximal end of a pull wire;
   a slider slidably disposed within the shell, said slider having a resting position, an intermediate position and a deployment position, the slider movable among said positions, the slider also having a trip; and
   a shuttle slidably disposed within the shell and coupled to the slider by a first energy storage member, said shuttle having a resting position and a deployment position, the shuttle movable among said positions, the shuttle comprising a latch member that is releasably retained by the stop element, said latch member releaseable by the trip, the shuttle further comprising a wire gripper for engaging a pull wire; wherein the shuttle remains in said resting position during proximal retraction of the slider, storing potential energy in the first energy storage member, until the trip engages the latch and releases the latch from the stop element thereby allowing the shuttle to be pulled proximally by the first energy storage member to the shuttle's deployment position.

2. The handle according to claim 1 wherein when said slider is in said resting position or said intermediate position, said shuttle is in said resting position.

3. The handle according to claim 1 wherein said slider and said shuttle return to their respective resting positions following release of said slider from said deployment position.

4. The handle according to claim 1 wherein said shuttle latch member further comprises a button, whereby said button rests against said stop when said shuttle is in said resting position, and wherein said button is depressed by said slider when said slider is in said deployment position, whereby said button no longer rests against said stop.

5. The handle according to claim 1 further comprising a compression spring, where said first energy storage member biases said shuttle into said deployment position and said compression spring biases said slider and shuttle to their respective resting positions.

6. The handle according to claim 1 further comprising an internal lumen for receiving a pull wire.

7. The handle according to claim 1 wherein said wire gripper has a resting position and a gripping position.

8. The handle according to claim 1 wherein said slider prevents gripping of a pull wire by said wire gripper when said slider and said wire gripper are in their respective resting positions; and wherein when said slider is in said intermediate position, said wire gripper converts to said gripping position to grip a pull wire.

9. The handle according to claim 1 wherein said wire gripper comprises gripper elements and said slider comprises a wedge, wherein said wedge nests between said gripper elements when said slider is in said resting position.

10. The handle according to claim 9 wherein said gripper elements further comprise a pivot point, and wherein said gripper elements are pivotable about said pivot points to grip a pull wire, to release a pull wire, or to return said wire gripper to its resting position.

11. The handle according to claim 1 further comprising a thumb grip movably mounted thereupon and in communication with said slider.

12. The handle according to claim 1 further comprising a substantially hollow interior and wherein said slider and said shuttle are housed within said substantially hollow interior.

13. A system for deploying an implant, the system comprising:
   an implant;
   an implant tool including a shaft having a lumen;
   a pull wire having a proximal end and a distal end, the pull wire disposed within the lumen and movable from a first position to a second position for retaining the implant near the distal end of the pull wire, and then releasing the implant;
   a handle including a shell having a proximal end, a distal end, a stop element and a receptacle for receiving the pull wire; said handle also comprising a slider slidably disposed within the shell, a shuttle slidably disposed within the shell and coupled to the slider by a first energy storage member, and a trip, where said slider is movable among a resting position, an intermediate position and a deployment position, and said shuttle comprises a latch member releasably retained by said stop element, and a wire gripper, and said shuttle has a resting position and a deployed position, whereby when said slider is moved to its deployment position, said first energy storage member is stretched axially, thereby storing potential energy in said first energy storage member, until said shuttle is moved to its deployed position via said trip, which releases said latch member, the shuttle thereby retracting said pull wire and releasing said implant.

14. The system of claim 13 where said wire gripper converts from said resting position to said gripping position when said slider is in said intermediate position.

15. The system of claim 13 wherein said slider comprises a wedge and said wire gripper comprises gripper elements, and whereby said wedge prevents engagement of said gripper elements when said slider is in said resting position.

16. The system of claim 13 where said handle further comprises a compression spring for biasing said slider and said shuttle to return to their respective resting positions following release of said slider by a user.

* * * * *